US010709371B2

United States Patent
Kalra et al.

(10) Patent No.: US 10,709,371 B2
(45) Date of Patent: Jul. 14, 2020

(54) SYSTEM AND METHODS FOR SERVING A CUSTOM MEDITATION PROGRAM TO A PATIENT

(71) Applicant: WellBrain, Inc., Pleasant Hill, CA (US)

(72) Inventors: Ruben Kalra, Pleasant Hill, CA (US); William Longton, Pleasant Hill, CA (US); Richard Shinaman, Pleasant Hill, CA (US)

(73) Assignee: WellBrain, Inc., Pleasant Hill, CA (US)

( * ) Notice: Subject to any disclaimer, the term of this patent is extended or adjusted under 35 U.S.C. 154(b) by 580 days.

(21) Appl. No.: 15/260,422

(22) Filed: Sep. 9, 2016

(65) Prior Publication Data

US 2017/0188976 A1 Jul. 6, 2017

Related U.S. Application Data

(60) Provisional application No. 62/216,313, filed on Sep. 9, 2015.

(51) Int. Cl.
*A61B 5/16* (2006.01)
*G16H 10/20* (2018.01)
(Continued)

(52) U.S. Cl.
CPC .............. *A61B 5/165* (2013.01); *A61B 5/486* (2013.01); *A61B 5/4854* (2013.01);
(Continued)

(58) Field of Classification Search
CPC .............................. G16H 50/20; G16H 10/20
See application file for complete search history.

(56) References Cited

U.S. PATENT DOCUMENTS

| 6,425,764 B1 * | 7/2002 | Lamson | A61M 21/00 434/236 |
| 2003/0135128 A1 * | 7/2003 | Suffin | A61B 5/0006 600/544 |

(Continued)

FOREIGN PATENT DOCUMENTS

WO 2015114629 A1 8/2015

OTHER PUBLICATIONS

Hoffman, "Meditation as an Adjunct Therapy in Treating Mental Illness", PsychCentral.com, Apr. 15, 2013, <URL: http://psychcentral.com/blog/archives/2013/04/15/meditation-as-an-adjunct-therapy-in-treating-mental-illness/ >.

(Continued)

*Primary Examiner* — David L Lewis
*Assistant Examiner* — Shauna-Kay Hall
(74) *Attorney, Agent, or Firm* — Run8 Patent Group, LLC; Peter Miller

(57) ABSTRACT

One variation of a method for addressing psychological conditions of a patient through guided meditation includes: serving a first psychological test to the patient through a virtual patient portal; transforming results of the first psychological test into a set of psychological conditions of the patient; matching a first predefined meditation path to the patient based on a severity of each psychological condition in the set of psychological conditions; serving a first guided meditation track in the first meditation path to the patient through the virtual patient portal; serving a second psychological test to the patient through the virtual patient portal; calculating new intensities of each psychological condition in the set of psychological conditions of the patient based on results of the second psychological test; and matching a second predefined meditation path to the patient based on (Continued)

the new intensities of each psychological condition in the set of psychological conditions.

20 Claims, 7 Drawing Sheets

(51) Int. Cl.
  *G16H 50/20*   (2018.01)
  *A61B 5/00*   (2006.01)
(52) U.S. Cl.
  CPC ........... *A61B 5/7264* (2013.01); *G16H 10/20* (2018.01); *G16H 50/20* (2018.01)

(56) References Cited

U.S. PATENT DOCUMENTS

| | | | |
|---|---|---|---|
| 2003/0167149 A1* | 9/2003 | Simon | A61B 5/16 702/182 |
| 2005/0007884 A1 | 1/2005 | Lorenzato | |
| 2006/0189878 A1* | 8/2006 | Joshi | G06Q 99/00 600/529 |
| 2006/0247489 A1* | 11/2006 | Carbis | A61M 21/00 600/27 |
| 2008/0071573 A1 | 3/2008 | Owens et al. | |
| 2008/0221920 A1* | 9/2008 | Courtney | G16H 10/65 705/2 |
| 2011/0245633 A1 | 10/2011 | Goldberg et al. | |
| 2012/0278093 A1* | 11/2012 | Amundson | G06Q 50/22 705/2 |
| 2014/0316230 A1* | 10/2014 | Denison | A61B 5/04012 600/383 |
| 2014/0347265 A1* | 11/2014 | Aimone | G09G 3/003 345/156 |
| 2015/0017618 A1 | 1/2015 | Portenga | |
| 2015/0046465 A1* | 2/2015 | Lambert | G01N 33/50 707/741 |
| 2015/0112208 A1 | 4/2015 | He et al. | |
| 2015/0199010 A1* | 7/2015 | Coleman | A61B 5/0006 345/156 |
| 2015/0351655 A1* | 12/2015 | Coleman | A61B 5/0482 600/301 |
| 2016/0077547 A1* | 3/2016 | Aimone | G06F 3/012 345/8 |
| 2017/0162072 A1* | 6/2017 | Horseman | G09B 19/00 |
| 2017/0304585 A1* | 10/2017 | Goldberg | A61M 21/02 |
| 2017/0333666 A1* | 11/2017 | Goldberg | A61B 5/02438 |

OTHER PUBLICATIONS

Kotz, "Can meditation top medication?", Boston Globe, Jan. 13, 2014 <URL: https://www.bostonglobe.com/lifestyle/health-wellness/2014/01/13/can-meditation-treat-anxiety-better-than-medication/ZV9bK3upScZQr879sI7xaK/story.html>.

\* cited by examiner

S100

*PainBrain Psychological Report*

---

*Patient Name: S STOUT*
*DOB: 1/19/1957*
*Average Mindfulness Exercise: 47%*
*Number of assessments: 5*

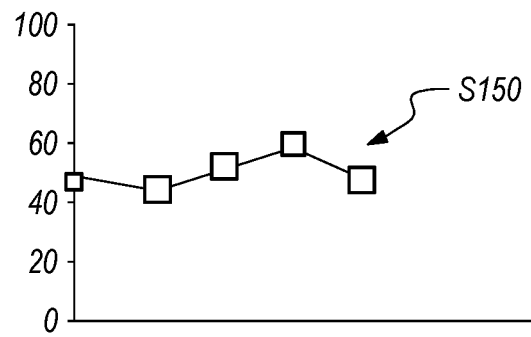

*03-13-2015 11:05 Mindfulness Exercise 47% NEEDS IMPROVEMENT*

---

*Guided meditation was administered to the patient today*

---

*Mindfulness Exercise Score Scale:*

*Greater than 65%: VERY MINDFUL, EXCELLENT EXERCISE SESSION*

*50% - 65%: MODERATELY MINDFUL, GOOD EXERCISE SESSION*

*Less than 50%: NEEDS IMPROVEMENT IN MINDFULNESS*

FIG. 7

SYSTEM AND METHODS FOR SERVING A CUSTOM MEDITATION PROGRAM TO A PATIENT

CROSS-REFERENCE TO RELATED APPLICATIONS

This application claims the benefit of U.S. Provisional Application No. 62/216,313, filed on 9 Sep. 2015, which is incorporated in its entirety by this reference.

TECHNICAL FIELD

This invention relates generally to the field of symptom management and more specifically to new and useful methods addressing psychological conditions of a patient through guided meditation in the field of symptom management.

BRIEF DESCRIPTION OF THE FIGURES

FIG. 7 is a graphical representation of one variation of the method.

DESCRIPTION OF THE EMBODIMENTS

The following description of the embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
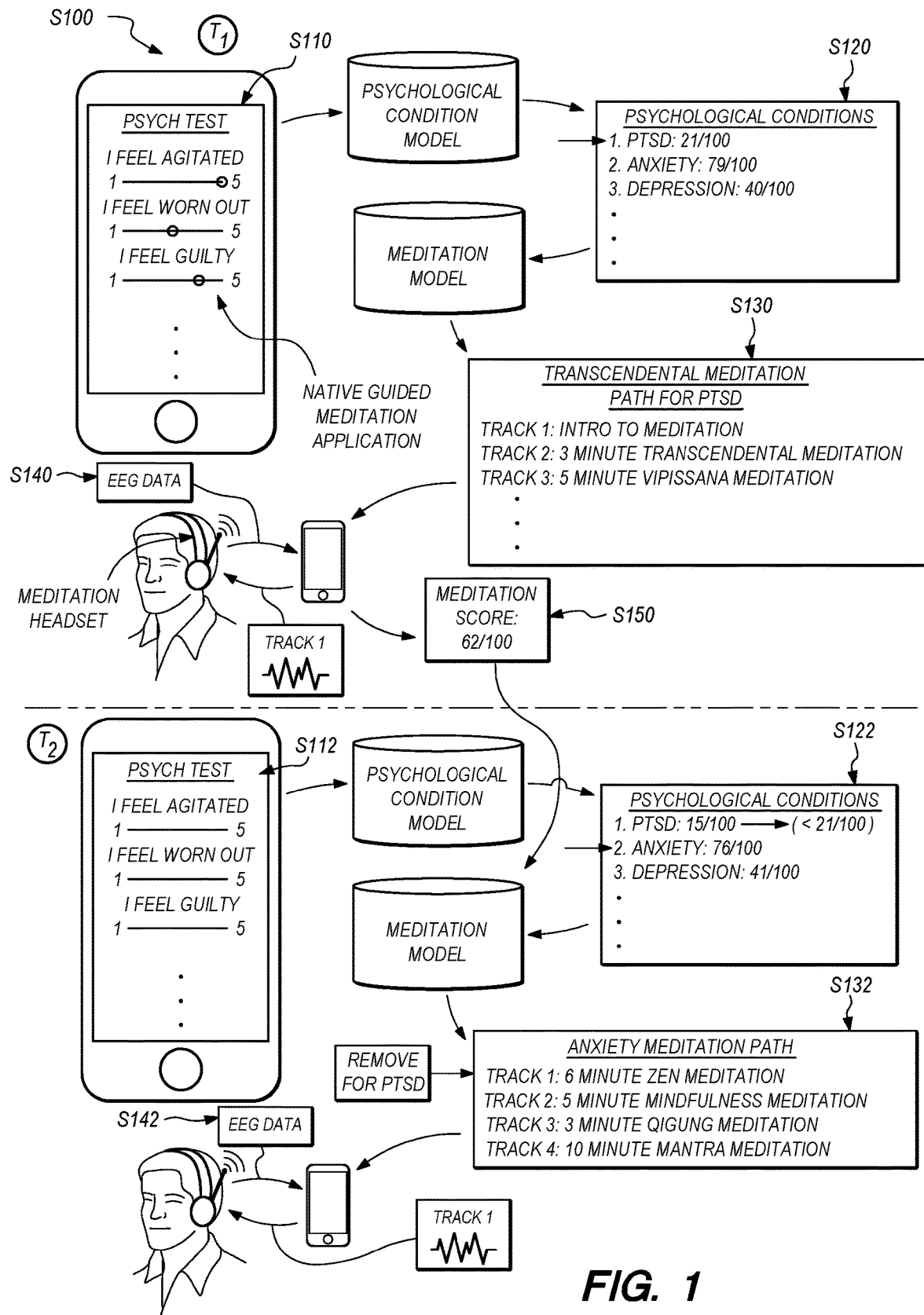
FIG. 1 is a flowchart representation of a method.
Figure 4:
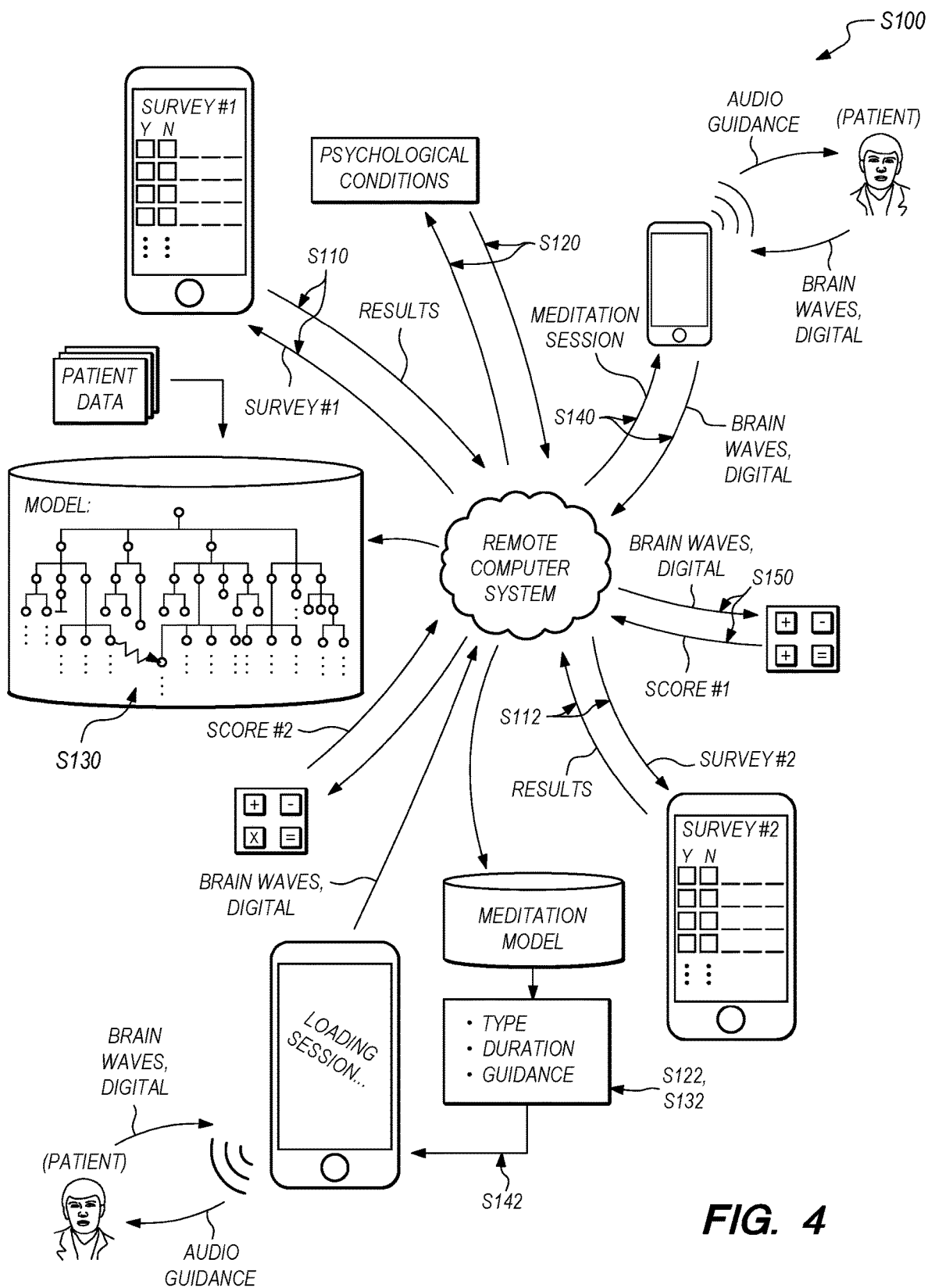
FIG. 4 is a flowchart representation of a method.

As shown in FIGS. 1 and 4, a method for serving a custom meditation program to a patient includes: assigning a first psychological test to the patient in Block S130; serving a first meditation track to the patient in Block S140; generating a first score for a meditative state of the patient during the first meditation track in Block S150; issuing a second psychological test to the patient in Block S112; defining a meditation type, duration, and guidance parameters for a second meditation track based on results of the first psychological test, results of the second psychological test, and the first meditation score in Block S132; serving the second meditation track to the patient in Block S142; generating a second score for a meditative state of the patient during the second meditation track in Block S150; and modifying a meditation model based on results of the first psychological test, results of the second psychological test, the first meditation score, and the second meditation score in Block S170, the meditation model defining relationships between meditation types, durations, and guidance parameters and patient feedback across a patient population.

As shown in FIG. 1, one variation of the method—for addressing psychological conditions of a patient through guided meditation—includes: serving a first psychological test to the patient through a virtual patient portal executing on a computing device in Block S110; transforming results of the first psychological test into a set of psychological conditions of the patient in Block S120; matching a first meditation path, from a set of predefined meditation paths, to the patient based on a severity of each psychological condition in the set of psychological conditions in Block S130; at a first time, serving a first guided meditation track in the first meditation path to the patient through the virtual patient portal in Block S140; at a second time succeeding completion of the first meditation path by the patient, serving a second psychological test to the patient through the virtual patient portal in Block S112; calculating new intensities of each psychological condition in the set of psychological conditions of the patient based on results of the second psychological test in Block S122; matching a second meditation path, from the set of predefined meditation paths, to the patient based on the new intensities of each psychological condition in the set of psychological conditions in Block S132; and at a third time succeeding the second time, serving a second guided meditation track in the second meditation path to the patient through the virtual patient portal in Block S142.

As shown in FIG. 1, another variation of the method includes: serving a first psychological test to the patient through a virtual patient portal executing on a computing device in Block S110; transforming intensities of psychological conditions represented in results of the first psychological test into a first rank set of psychological conditions of the patient in Block S120; matching a first meditation path from a set of predefined meditation paths to the patient in Block S130, the first meditation path configured to address a first psychological condition in the first rank set of psychological conditions; at a first time, serving a first guided meditation track in the first meditation path to the patient through the virtual patient portal in Block S140; transforming electroencephalogram data output by an electroencephalogram headset worn by the patient during completion of the first guided meditation track into a meditation score of the patient in Block S150; at a second time succeeding completion of the first meditation path by the patient, serving a second psychological test to the patient through the virtual patient portal in Block S112; transforming intensities of psychological conditions represented in results of the second psychological test into a second rank set of psychological conditions of the patient in Block S122; in response to a second psychological condition in the second ranked set of psychological conditions outranking the first psychological condition, matching a second meditation path from the set of predefined meditation paths to the patient in Block S132, the second meditation path configured to address the second psychological condition and representing a difficulty level corresponding to the meditation score of the patient; and at a third time succeeding the second time, serving a second guided meditation track in the second meditation path to the patient through the virtual patient portal in Block S142.

Figure 2:
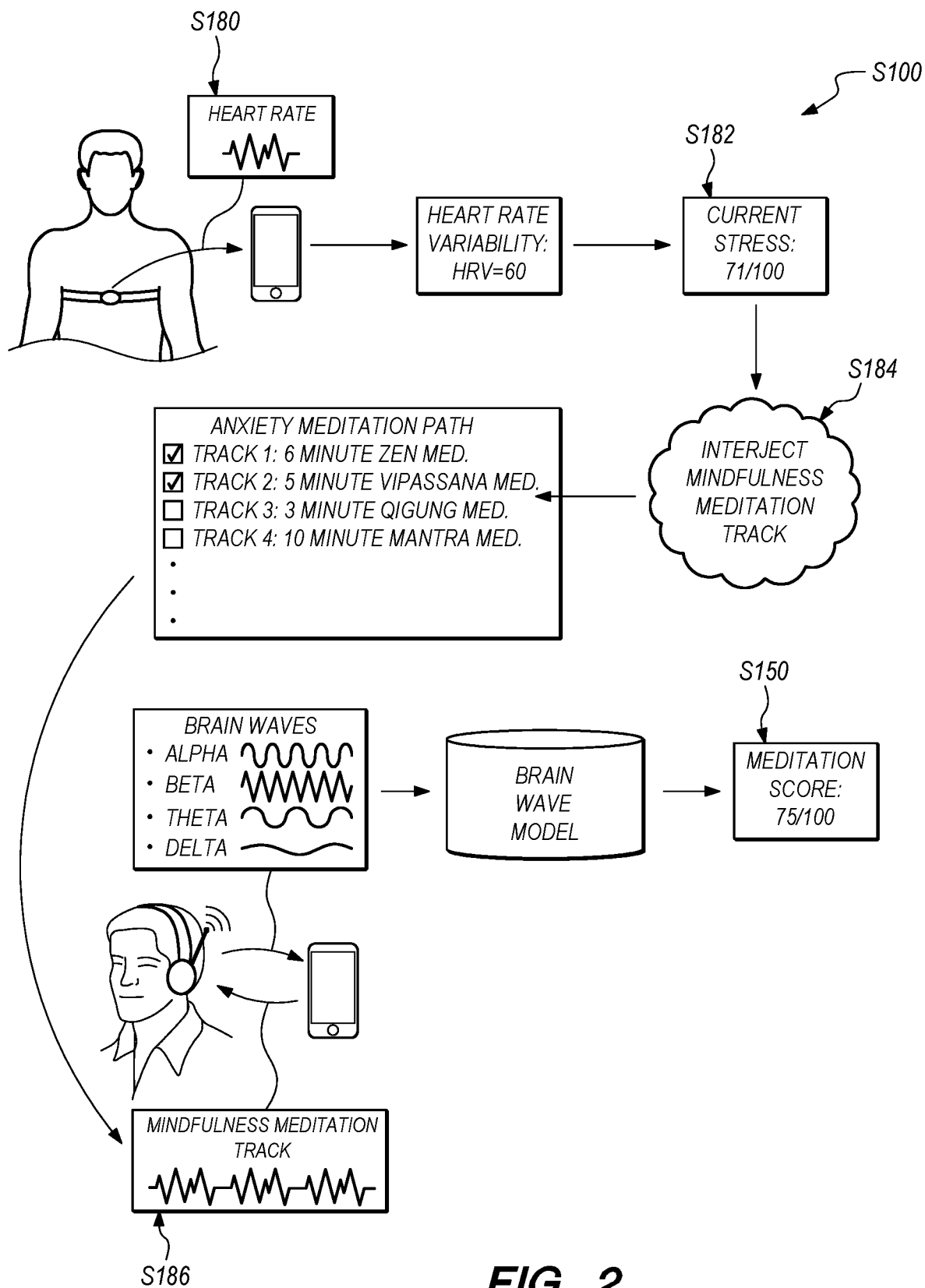
FIG. 2 is a flowchart representation of one variation of the method.

As shown in FIGS. 1 and 2, another variation of the method includes: serving a first psychological test to a patient in Block S110; transforming results of the first psychological test into a set of psychological conditions of the patient in Block S120; matching a first meditation path, from a set of predefined meditation paths, to the patient based on a severity of each psychological condition in the set of psychological conditions in Block S130, the first meditation path comprising an ordered set of guided meditation tracks addressing a psychological condition in the set of psychological conditions; at a first time, serving a first guided meditation track within the first meditation path to the patient through a virtual patient portal executing on a computing device in Block S140; at a second time succeeding the first time, accessing a current biometric signal of the patient in Block S180; mapping the current biometric signal of the patient to a current physiological state of the patient in Block S182; selecting an alternate guided meditation track outside of the first meditation path based on an intensity of the current physiological state of the patient in Block S184; and, at approximately the second time, serving the alternate guided meditation track in place of a second guided meditation track within the first meditation path through a virtual patient portal executing on the computing device in Block S186.

2. Applications

Generally, the method can be executed by a computer system (described below) to identify psychological conditions (e.g., psychological disorders) affecting a patient based on results of a psychological test, to assign a first set of guided meditation tracks (hereinafter a "meditation path") to the patient to address a primary psychological condition affecting the patient, and to determine an effectiveness of the first meditation path in addressing the patient's primary psychological condition, such as by reducing symptoms related to the primary psychological condition or providing the patient skills for managing the primary psychological condition. For example, once the patient has completed the first meditation path, the system can serve a second psychological test to the patient, identify changes in intensities of psychological conditions affecting the patient, and correlate these severity changes with effectiveness of the first meditation path, as shown in FIG. 1. The system can also transform electroencephalography (EEG) data collected through an EEG headset worn by the patient during completion of a meditation track within the first meditation path into a quantitative or qualitative meditation score indicative of the patient's meditation skills, as shown in FIG. 2.

Based on the effectiveness of the first meditation path, the system can later: assign a second set of guided meditation tracks to the patient to address a second psychological condition affecting the patient if the first meditation path is shown to be sufficiently effective in addressing the patient's primary psychological condition; or assign a different set of guided meditation tracks to the patient to address the primary psychological condition in a different way or to provide additional meditation guidance if the first meditation path is shown to be less effective in addressing the patient's primary psychological condition.

The system can therefore implement closed-loop controls to select and assign meditation tracks to a patient over time, according to the method, to address psychological conditions affecting the patient, such as anxiety, depression, substance abuse, physical pain, and/or post-traumatic stress disorder ("PTSD"), etc. The system can also rank or prioritize a patient's psychological conditions, such as based on known relationships between various psychological conditions and intensities of these conditions within the patient as determined from various psychological tests served to the patient. For example, for a patient experiencing pain, anxiety, depression, and PTSD, the system can prioritize PTSD over all other psychological conditions, then anxiety, and then pain and assign—to the patient—meditation paths that address these conditions in this order as additional psychological tests indicate that intensities of these psychological conditions are lessening in the patient.

The method can be implemented in conjunction with a medical facility or medical group—such as a hospital, doctor's office, pain management clinic, psychotherapist office, etc.—to automatically collect mental health data for a patient through verified psychological tests, to automatically prioritize psychological conditions affecting the patient based on results of these psychological tests, and to automatically prescribe and serve meditation paths to the patient to address these psychological conditions without (or in combination with) prescription medications. For example, a system executing Blocks of the method can prescribe meditation tracks of various types and durations to patients over time to address a patient's pain without prescription opioids, to address a patient's anxiety or sleep disorder without prescription central nervous system depressants, and to address a patient's attention-deficit/hyperactivity disorder or narcolepsy without prescription stimulants. The system can also execute Blocks of the method outside of a medical facility or medical group, such as in a patient's home or office, in order to guide the patient in addressing psychological conditions affecting her, to collect feedback from the patient (e.g., in the form of EEG or other biometric data or in the form of additional psychological tests), and to customize future meditation paths for the patient.

The system can also track a patient's meditation skills based on EEG data, heart rate data, heart rate variability, and/or other biometric data collected from the user during completion of a prescribed meditation track, generate a meditation score from these data, and serve this score to the patient in order to encourage the patient to improve her meditation skills. The system can also customize meditation paths with meditation tracks containing degrees of guidance matched to the patient's meditation skill level, as estimated from biometric data collected from the patient during completion of past meditation tracks.

3. System

Figure 5:
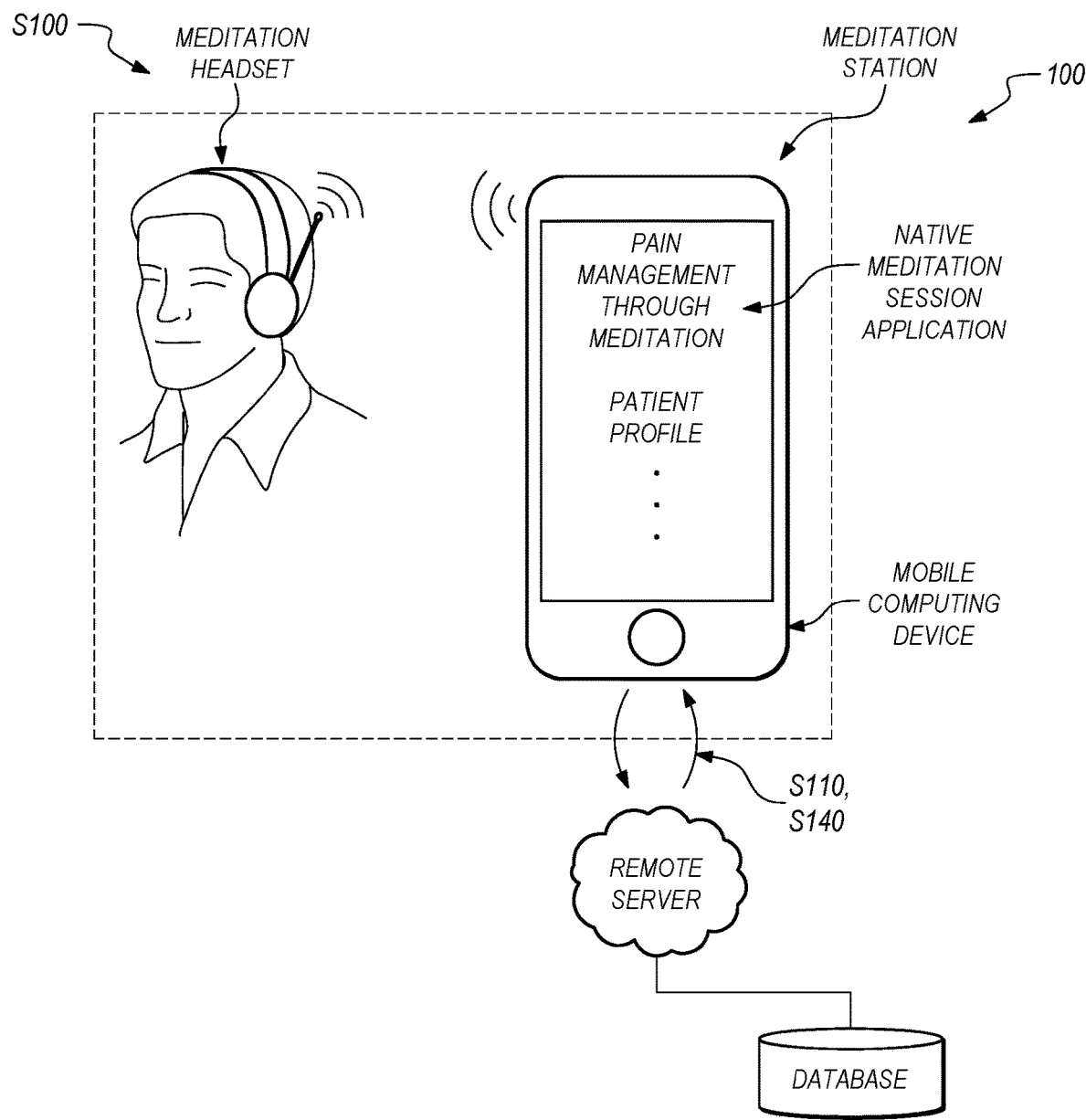
FIG. 5 is a schematic representation of a system.

As shown in FIG. 5, a system can execute Blocks of the method locally or remotely from a patient. Generally, Blocks of the method can be executed by a remote computer system, a remote database, and a local meditation station executing a native guided meditation application. For example, the local meditation station can include a patient's personal computing device (e.g., a smartphone) executing an instance of the native guided meditation application or a doctor- or clinic-issued meditation headset (e.g., an EEG headset with speaker) paired with a tablet computer executing an instance of the native guided meditation application.

The remote computer system can include a remote server, a remote computer network, a distributed network, or any other suitable type of computer system. The remote computer system can: collect patient medical records data, patient psychological test results, and post-meditation feedback from patients, etc.; and can remotely manipulate psychological test results, meditation track results (e.g., EEG data), and patient feedback collected over time to select a next meditation path (or next meditation track) or to customize guided meditation parameters for a next meditation track for a patient within a patient population.

The remote database can store: psychological test results; meditation track results; patient demographic data; patient medical records; medical events; and/or doctor feedback regarding patient pain, pain management, and/or psychological condition improvements, etc. The database can store these data in a private medical record database for each patient or anonymize and store these data in a general database for a patient population or patient sub-population. The remote computer system can access these data collected over time to extrapolate correlations between the foregoing data types and patient outcomes and then modify a meditation track selection model (or multiple distinct meditation track selection models, such as demographic-specific meditation track selection models) over time based on these correlations.

As described above, the meditation station can include a (mobile) computing device—such as a smartphone or a tablet—executing a native guided meditation application. The meditation station also can include a meditation headset including: one or more electroencephalography (EEG) sensors configured to read a patient's alpha, beta, delta, and/or theta brain waves worn by the patient; an audio driver (e.g., a speaker) through which the meditation station outputs audible feedback and/or audible guidance from a meditation track performed by the patient; and a wireless communication module or a wired connection that transmits and receives data to and from the computing device, such as patient brain wave data and audio data from the current meditation track, respectively.

In the foregoing implementation, the native guided meditation application can handle distribution of meditation track data between the meditation headset and the remote computer system. The native guided meditation application can also incorporate a user interface for delivering digital psychological tests to a patient and collecting responses to these psychological tests from the patient. Alternatively, the computing device and the meditation headset can be integrated into a single device or distributed across multiple other devices, such as across the remote computer system and the meditation headset.

The method for addressing psychological conditions of a patient through guided meditation is described herein as executed by the system. Blocks of the method can be performed locally at the meditation station, such as by an instance of the native guided meditation application executing on a patient's private or clinic-issued mobile computing device configured to interface with a meditation headset. Blocks of the method can additionally or alternatively be performed remotely, such as by a remote server hosting the native guided meditation application. However, any other element within a local, remote, or distributed computer system can execute Blocks of the method described below.

4. Use Setting

An office assistant, nurse, doctor, clinician, therapist, or other on-site care provider can provide a meditation station to a patient while the patient waits in a waiting room, in an examination room, in a dedicated medication room, or in another space within a hospital, emergency room, medical clinic, or psychotherapy office, etc. The system can then serve a psychological test to the patient in Block S110, match the patient to a meditation path in Block S130, and then serve a meditation track to the patient through the meditation station in Block S140, as described below.

The system is described herein as implemented in a clinical setting with an inpatient meditation station to serve psychological tests to the patient and to serve meditation tracks of assigned meditation paths to a patient during office visits. However, the system can additionally or alternatively be implemented in conjunction with a consumer-based meditation station, with an outpatient clinical meditation station issued to and operated by a user (e.g., a patient) at home, in an office, or in any other non-clinical setting; or with a consumer-based native guided meditation application executing on the patient's personal computing device, or otherwise outside of a clinical setting. For example, Blocks of the method can be executed by a native guided meditation application executing on a user's personal smartphone or tablet, which can communicate wirelessly with the user's personal meditation headset to provide meditation guidance to the user during a meditation track selected for the patient locally by the native guided meditation application or selected for the patient remotely by a remote computer system and uploaded to the user's personal smartphone or tablet. In another example, a hospital, medical clinic, psychotherapy office, or other clinical institution can lease meditation stations to a patient in order to provide the patient with access to meditation guidance and in order to collect meditation data from this patient when not visiting the institution. In these examples, the meditation station can locally execute Blocks S120 and S130 to match a meditation path to the user based on results of a psychological test or receive a meditation path assigned to the patient by a remote computer system remotely executing Blocks S120 and S130 of the method; the meditation station can then serve meditation tracks from the assigned meditation path to the user in Block S140, as described below.

5. First Psychological Test

Block S110 of the method recites serving a first psychological test to the patient through a virtual patient portal executing on a computing device. Generally, in Block S110, the system can serve a psychological test to the patient, such as through a virtual patient portal within the native guided meditation application executing on a tablet assigned to the patient or on the patient's personal smartphone. In particular, the system can serve a psychological test containing a set of questions to the patient, such as in the form of a short (e.g., two-minute, ten-minute) digital survey. The system can then transform responses provided by the patient in response to these questions into a possible presence or approximate severity of one or more psychological conditions that may affect the patient—such as PTSD, substance-abuse, physical pain, insomnia, anxiety, or depression, etc.—in Block S120. The system can then assign a meditation path to the patient in Block S130 to address one or more of these psychological conditions.

In one implementation, when a patient is first issued a meditation station, such as by a nurse or other care provider, the system can: prompt the patient to set up a patient account by providing identifying information; serve a first virtual psychological test to the patient through a computing device within the meditation station; and then record responses to questions in the psychological test entered by the patient through the computing device. For example, once the patient creates a patient account within the system, the system can serve to the patient a brief, generic psychological test—such as including a set of ten true or false questions and/or scale (e.g., on a scale of "1" through "10") related to the patient's mental condition, physical condition, and/or medical history—to the patient. In this example, the psychological test can include questions that generally assess the patient's anxiety, risk of depression, total pain level, and risk for opioid abuse.

Alternatively, the system can host multiple distinct validated psychological tests, such as including: a post-traumatic stress disorder test; an alcohol-abuse screening test; a substance-abuse screening test; a pain self efficacy test; an insomnia test; an opioid risk screening test; an anxiety test; a depression test; and a perceived stress test. For example, a doctor, nurse, or other care provider can access a care provider portal to select a particular psychological test—from this set of available psychological tests—to serve to the patient. In this example, the care provider can assign an opioid risk test to a patient exhibiting physical pain, currently prescribed painkillers, or scheduled for an upcoming surgery in order to test the patient's risk of abusing an opioid painkiller. The system can then serve this single, targeted psychological test to the patient through the virtual patient portal in Block S110. The system can also serve multiple distinct psychological tests sequentially to the patient, such as if the patient's care provider elects to test the patient for multiple psychological conditions. Similarly, the system can compile multiple psychological tests elected by the patient's care provider into one composite test and then serve this composite psychological test to the patient in order to test the patient for multiple psychological conditions in one psychological test.

Yet alternatively, the system can serve to the patient a dynamic psychological test in which each subsequent question served to the patient is selected from a question tree based on a response provided by the patient in response to a previous question. The system can thus navigate through a sequence of increasingly pointed questions to identify the presence and/or severity of a variety of psychological conditions that may be affecting the patient.

However, the system can implement any other method or technique to serve a psychological test containing questions in any other format to the patient.

6. First Set of Psychological Conditions

Block S120 of the method recites transforming results of the first psychological test into a set of psychological conditions of the patient. Generally, in Block S120, the system can record responses entered by the patient through the patient portal and can calculate one or more scores for the patient's anxiety, depression, total pain level (e.g., Oswestry score), and/or risk for opioid abuse, etc. based on the patient's responses. The system can also package and present these scores to a doctor, nurse, or other staff at the clinic before the patient is examined, such as to provide guidance to the doctor, nurse, or other care provider when selecting a therapy or medication for the patient.

In one implementation, the system serves a validated psychological test to the patient in Block S110 and then implements a scoring model associated with the psychological test to automatically calculate a quantitative or qualitative severity of a psychological condition—tested by the psychological test—affecting the patient. For example, the system can serve a depression test to the patient in Block S110 and then score the patient as exhibiting "no depression," "mild depression," "moderate depression," "moderately severe depression," or "severe depression" in Block S120. In another example, the system can serve an anxiety test to the patient in Block S110 and then score the patient as exhibiting anxiety on a scale of "1" for "at ease" to "10" for "panicked" in Block S120.

In implementations in which the system serves a psychological test configured to test multiple psychological conditions or in which the system serves multiple psychological tests to the patient in Block S110, the system can implement similar methods and techniques to calculate a score or severity for each psychological condition tested in Block S110. However, the system can implement any other methods or techniques to transform results of a psychological test served to the patient into a score or severity of one or more psychological conditions possibly affecting the patient.

7. First Meditation Path

Block S130 of the method recites matching a first meditation path, from a set of predefined meditation paths, to the patient based on a severity of each psychological condition in the set of psychological conditions. Generally, in Block S130, the system prescribes a meditation path—containing one or more meditation tracks matched to psychological condition scores calculated in Block S120—to the patient. In particular, the system can identify one or more psychological conditions of sufficient severity to noticeably negative the patient based on results of the psychological test, prioritize these psychological conditions based on type and/or severity, and then select (or generate) a meditation path designed to address one or more of these psychological conditions in order of priority.

In one implementation, the system implements template matching techniques to match a result of the first psychological test directly to a particular template psychological test result—from a prepopulated suite of template psychological test results—and then prescribes (or assigns, matches) a particular meditation path associated with the particular template psychological test result to the patient in Block S130. For example, each template psychological test result in the suite can define a specific response (e.g., true for a true or false, "4" on a scale of "1" to "10" for a scale question) for each question in the first psychological test, and the system can match the patient's psychological test results to a particular template psychological test result only if the patient's psychological test results match the particular template psychological test result exactly. Alternatively, each template psychological test result in the suite can define a range of possible responses (e.g., "4" or "5" on a scale of "1" to "10" for a scale question) for each question in the first psychological test, and the system can match the patient's psychological test results to a particular template psychological test result if all responses entered by the patient fall within a range specified in the particular template psychological test result for the corresponding question. Each template psychological test result can be paired with a meditation path—such as a meditation path containing a unique sequence of guided meditation tracks configured to address a particular psychological condition or combination of psychological conditions in a particular way—and the system can assign a particular meditation path to the patient in Block S130 responsive to a suitable match between the patient's responses to the first psychological test and a template psychological test result for the same psychological test.

In a similar implementation, the system implements template matching techniques to match a combination of psychological conditions and their intensities—calculated from results of the first psychological test in Block S120—to a particular template psychological test result paired with a particular meditation path and then assigns the particular meditation path to the patient in Block S130. For example, the system can retrieve a set of template psychological test results corresponding to a range of available psychological test in a template database, wherein each template psychological test result defines a specific severity or range of intensities for one or more psychological conditions tested in one of the available psychological tests. In this example, the system can access the template database, retrieve a subset of template psychological test results corresponding to the psychological test served to the patient in Block S110, and identify a particular template psychological test result defining psychological condition intensities nearest those calculated from the patient's test results in Block S120. The system can then prescribe the patient a particular meditation path associated with the matched template psychological test result in Block S130.

In another implementation, the system can rank psychological conditions identified in Block S120 by type and severity and then select a predefined meditation path configured to specifically address a primary psychological condition in this ranked set of psychological conditions. In one example, the system ranks psychological conditions by severity, including ranking a highest-severity psychological condition first and a lowest-severity psychological condition last. The system can also apply trump rules to prioritize certain psychological conditions over others (substantially) regardless of severity. In the foregoing example, the system can: prioritize any detectable PTSD condition over all other conditions; prioritize any anxiety condition greater than or equal to moderate anxiety over all other psychological conditions other than a PTSD condition; and otherwise rank the patient's psychological condition by severity.

In a similar example shown in FIG. 1, the system can implement a psychological condition model that defines a hierarchy of psychological conditions by type and severity range. In this example, the psychological condition model can rank psychological conditions in order as follows: 1) PTSD exhibited; 2) moderate or greater anxiety exhibited; 3) severe depression exhibited; 4) mild anxiety exhibited; 5) moderate to moderately severe depression exhibited; 6) moderate or greater pain exhibited; 7) any substance abuse exhibited; 8) mild depression exhibited; and 9) mild pain exhibited, etc. However, the system can store such a set of psychological condition rankings in a decision tree or any other data format.

As shown in FIG. 1, the system can pass results of the first psychological test through this psychological condition model in order to rank psychological conditions affecting the patient, and the system can then prescribe a meditation path associated with the patient's primary psychological condition in Block S130. For example, the system can select a first, standard, or default meditation path configured (e.g., by a care provider or automatically based on meditation path results, as described below) to address the patient's primary psychological condition in Block S130. Alternately, the system can select a meditation path configured to address primary and secondary psychological conditions in the ranked set. Yet alternatively, the system can also select a particular meditation path—from a prepopulated group of meditation paths—configured to address a ranked list of psychological conditions best approximating the ranked set of the patient's psychological conditions.

Furthermore, each predefined meditation path configured to address a particular psychological condition can also be associated with an historical success rate for patients of various demographics, such as age, gender, occupation, and/or education level. In instances in which the system identifies multiple predefined meditation paths that match the patient's primary psychological condition, the system can filter these available meditation paths by patient demographic data in order to select a particular meditation path most likely—according to past results—to yield a reduction in the severity of the patient's primary psychological condition upon completion of the particular meditation path by the patient.

Each predefined meditation path can include multiple guided meditation tracks, such as ten meditation tracks five minutes to fifteen minutes in length. Each meditation track can include an audio track containing voice instructions and/or symbolic cues to guide the patient through a particular type of meditation or mindfulness training. A predefined meditation path can also include one or more meditation teaching modules, such as in the form of an instructional video, designed to teach the patient how to meditate or how to achieve a state of mindfulness, to provide tips for meditating, or to inform the patient about the relevance of the meditation track or meditation path to a particular psychological condition affecting the patient, etc. However, a meditation path can include any other type or number of meditation tracks or meditation teaching modules.

8. Custom Meditation Path

In one variation, the system populates a meditation path with a custom set of meditation tracks based on results of the first psychological test. In one example, in Block S110, the system can: incorporate the question, "Are you experiencing chronic pain?" into the first psychological test presented to the patient through the virtual portal; open a virtual two-dimensional image of a human body within the virtual portal; prompt the patient to select one or more regions on the image corresponding to where the patient is experiencing chronic pain; and record this body region in the patient's profile. In Block S130, the system can insert a Vipassana meditation track—containing guidance for building tools for managing this pain—into the first meditation path. In this example, the system can also: prompt the patient to rate her pain on a scale of 1 to 10, such as by manipulating a slider bar; and then prioritize treatment of mental and physical ailments with select meditation tracks based on physical pain levels and degrees of psychological conditions. In this example, if the patient's response to the first psychological test indicates high anxiety, chronic back pain associated with a patient-entered pain level of 8/10, and knee pain associated with a patient-entered pain level of 5/10, the system can serve a first meditation track to provide the patient with tools for coping with and managing her lower back pain (which may be one factor in the patient's anxiety), followed by a second meditation track to address and reduce the patient's anxiety, which is then followed by a third meditation track to address the patient's knee pain as the patient progresses through a meditation program in a single clinical visit and/or over a period of several weeks, months, or years. In Block S130, the system can thus populate one meditation track within a set of meditation tracks customized for the patient based on results of the first psychological test.

The system can also serve additional psychological tests to the patient between completion of one meditation track and selection of a subsequent meditation track in order to continually refine and customize meditation tracks for the patient based on the patient's changing mental and physical conditions over time. Therefore, in this variation, the system can select a first meditation track—from a set of available meditation tracks—to specifically address the patient's mental and/or physical health status as determined from the patient's responses to the first psychological test.

9. Generic First Meditation Path

Alternatively, for the first meditation path served to the patient following creation of the patient's profile within the system, the system can select a standard, generic meditation path suited both to patients who have not previously meditated and to those with some or significant experience in meditation for the first meditation path. For example, in Block S130, the system can select a first meditation path containing meditation tracks that cooperate to define a generic meditation primer for patients with no or minimal meditation experience; during completion of meditation tracks in this first meditation path, the system can capture baseline data for the patient's meditation capacity and receptiveness to meditation. For example, the system can; generate a first meditation path containing an introductory five-minute mindfulness meditation track for that patient after the patient first activates a meditation account. The system can later implement methods and techniques described above and below to select a second meditation path tailored more specifically to the patient's current psychological condition based on meditation data collected from the patient during completion of the first meditation path and based on a second psychological test served to the patient after completion of the first meditation path.

10. Serving a First Meditation Track

Figure 3:
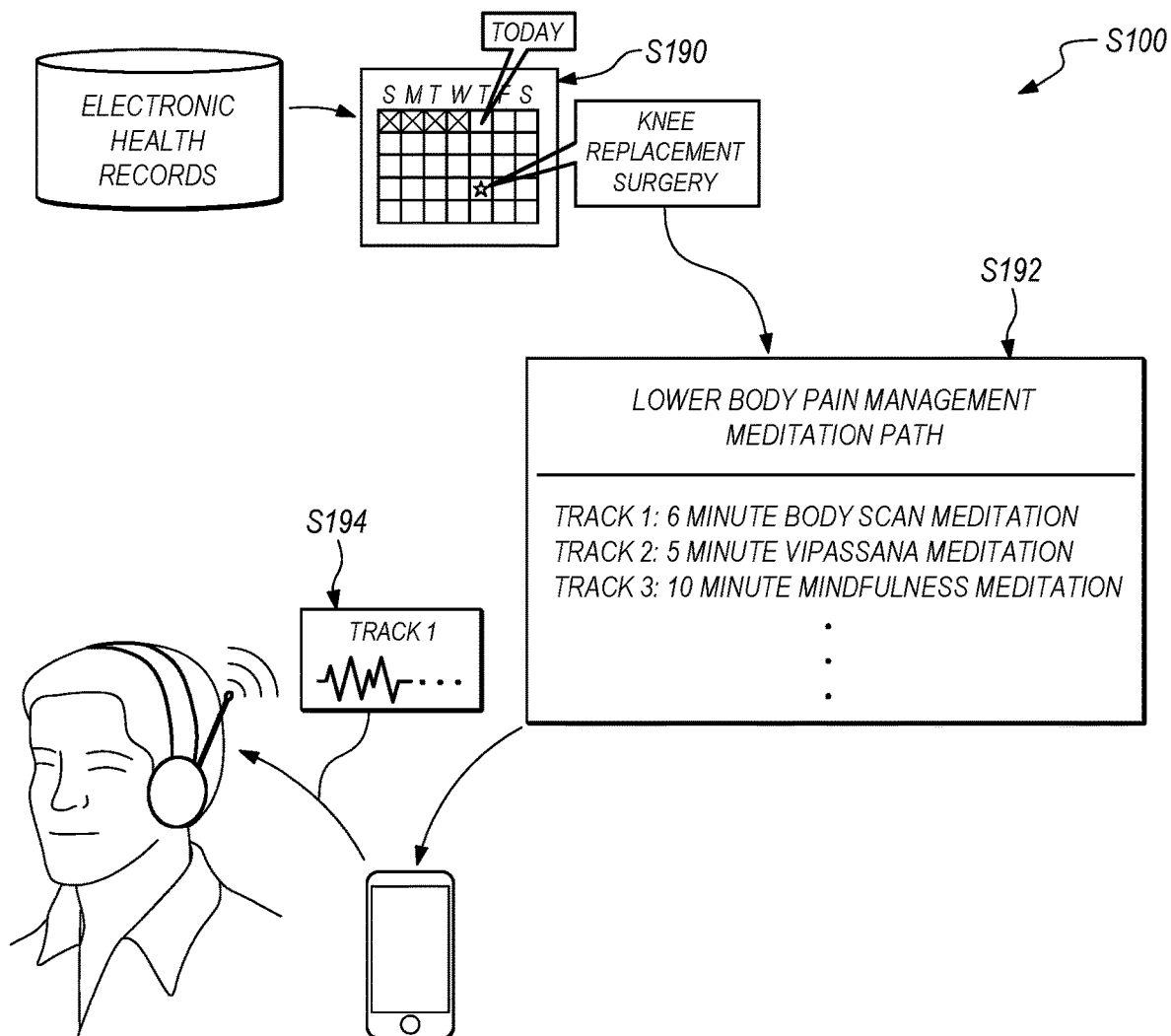
FIG. 3 is a flowchart representation of one variation of the method.

Block S140 of the method recites, at a first time, serving a first guided meditation track in the first meditation path to the patient through the virtual patient portal. Generally, in Block S140, the system serves a first meditation track in the first meditation path to the patient, such as through the meditation headset containing a speaker or through a set of headphones connected to a mobile computing device executing the native guided meditation application, as shown in FIGS. 1, 2, and 3.

In one implementation, the mobile computing device executing the native guided meditation application passes the patient's psychological test responses to the remote computer system, such as over the Internet or local area network connection. The remote computer system processes the patient's responses as described above to select the first meditation path for the patient and then returns a first meditation track in the first meditation path to the mobile computing device. The mobile computing device can then replay audio content from the first meditation track through the meditation headset or through a set of headphones connected to the mobile computing device, such as via a wired connection or over wireless communication protocol, in order to provide the patient with audible guidance while completing the meditation track.

The system can sequentially serve each guided meditation track in the first meditation path through the virtual patient portal as the patient completes each successive guided meditation track. For example, upon completion of the first meditation track, the system can prompt the patient to confirm a second meditation track and can then implement methods and techniques described above to serve the second meditation track to the patient. In another example, the system can serve a meditation track prompt to the patient every morning or every morning and evening at times selected by the patient and sequentially serve meditation tracks within the current meditation path to the patient according to the patient's response.

11. Meditation Score

As shown in FIG. 2, one variation of the method includes Block S150, which recites calculating a meditation score for a patient during completion of a meditation track. Generally, in Block S150, the system can collect biometric data from the patient while the patient preforms an assigned meditation track and then transforms these biometric data into a meditation score representative of a degree of the patient's mindfulness or meditative state over the total meditation track or at distinct instances during the meditation track. The system can later serve a meditation score to the patient to instigate the patient's improvement in her meditation skills. The system can additionally or alternatively select a second meditation path for the patient at a later date based on the patient's meditation score, such as to match a difficulty of meditation tracks or an entire meditation path to the patient's meditation skills, as indicated by the patient's meditation score.

In one implementation, the system accesses electroencephalogram data collected output by an electroencephalogram ("EEG") headset worn by the patient during completion of the first guided meditation track and transforms these data into a meditation score, such as on a scale of "1" to "100," in Block S150. In this implementation, the meditation headset can include one or more EEG electrodes configured to sense fluctuating electrical voltage potential(s) across a patient's scalp when worn by the patient. For example, the meditation headset can regularly sample integrated EEG electrodes, such as at a rate of 100 Hz, to collect a fluctuating voltage potential signal at each electrode. The meditation headset can transmit these voltage potential signals in digital form and substantially in real-time to a connected mobile computing device executing the native guided meditation application, such as over a wired or wireless connection. At the mobile computing device, the native guided meditation application can implement Fourier analysis or other techniques to transform these voltage potential signals into discrete brain wave signals, such as alpha, beta, theta, and/or delta brain wave signals. The native guided meditation application can then characterize the patient's meditative state throughout the meditation track or at specific instances during the meditation track based on absolute or relative magnitudes of these brain wave signals. For example, the native guided meditation application can calculate a quantitative meditation score that is inversely proportional to a magnitude of alpha waves read by the meditation headset at a particle instance in time (e.g., for one sampling period). The native guided meditation application can repeat this process for each sampling period (or sequence of sampling periods) through the meditation track; the native guided meditation application can also combine (e.g., average) meditation scores for the duration of the meditation track into a single composite score.

In the foregoing implementation, the native guided meditation application can calculate a meditation score for the patient and respond to this meditation score substantially in real-time. For example, the native guided meditation application can selectively output audible guidance, such as in the form of a recorded voice or a chime, to guide the patient back into a meditative state if the patient's current meditation score is below a threshold value or if a past sequence of meditation scores indicate that the patient is fluctuating in and out of a meditative state, is exiting a meditative state, or is approaching a meditative state. However, the native guided meditation application can selectively serve any other type of feedback to the patient in real-time during completion of a meditation track in any other way based on real biometric (e.g., EEG) data collected from the patient.

The native guided meditation application can also serve a composite meditation score (e.g., a numerical value) to the patient upon completion of the meditation track, such as through the virtual patient portal within the native guided meditation application. Similarly, the native guided meditation application can aggregate meditation scores calculated throughout the meditation track into a time-dependent chart and similarly present this chat to the patient, as shown in FIG. 7.

The system can also share the patient's meditation score with a doctor, therapist, or other care provider, such a through a care provider portal as described above. For example, the system can package results of the patient's first meditation path (or first meditation track) with results of the first psychological test and deliver this package to a doctor, nurse, or other care provider at a medical facility. For example, the system can generate a single graphical report including: the patient's opioid risk score, Oswestry score, anxiety score, and/or depression score based on results from the first psychological test; and the patient's average meditation score (e.g., on a scale of 1 to 100) across the first meditation path. The system can automatically push this graphical report to the care provider, as shown in FIG. 7. The doctor or other care provider may then prescribe physical therapy, emotion therapy, medication, and/or additional meditation paths to the patient based on these data.

The system can thus collect EEG data through an EEG headset worn by the patient during completion of a guided meditation track, such as during a visit to a medical clinic, hospital, or other medical setting, and transform these EEG data into a meditation score for the patient. The system can implement similar methods and techniques to collect other biometric data from the patient—such as heart rate, heart rate variability, or skin temperature—before, during, and/or after completion of a meditation track by the patient, and the system can implement similar methods and techniques to transform these biometric data into meditation scores.

12. Manual Patient Feedback

However, if the patient performs a guided meditation track while not wearing an EEG headset—such as when at home, at her office, or otherwise not in a medical setting or medical facility—the system can prompt the patient to provide manual feedback regarding her meditation experience and psychological condition following the meditation track, such as through a survey or second psychological test presented to the patient through the virtual patient portal within the native guided meditation track executing on the patient's personal mobile computing device.

In one implementation, if the patient completes a meditation track without wearing a meditation headset or other device configured to detect a biometric signal of the patient, the system can serve a set of survey questions regarding the patient's perceived severity of a psychological condition—identified previously from results of the first psychological test—to the patient through the virtual patient portal. For example, the system can serve an abbreviated psychological test to the patient after completion of each meditation track (and can serve a complete psychological test to the patient upon completion of a meditation path). The system can process responses entered by the patient to estimate an effectiveness of the meditation track in addressing a particular psychological condition and/or in providing the patient with a tool for managing symptoms of a psychological condition; the system can then modify a subsequent meditation track within the current meditation path based on these patient responses. Alternatively, the system can interpolate an effectiveness of the meditation path over time based on patient responses provided upon completion of each meditation track within the meditation path and then apply this interpolated effectiveness to selection of a next meditation path for the patient in Block S132 upon completion of the first meditation path.

However, the system can collect manual feedback from the patient in any other way between consecutive meditation tracks within one meditation path.

In one variation, upon completion of the first meditation track, the system selects or auto-generates a post-meditation survey that includes questions about the patient's experience during and/or after the first meditation track. In one example, if the patient's responses to the first psychological test indicate that the patient is experiencing anxiety and the system serves a first meditation track to target the patient's anxiety, the system can serve one or more anxiety-related questions to the patient in the post-meditation survey, such as, "Are you feeling more calm after your first meditation track?" and/or "Have you noticed any positive change in your anxiety level since your first meditation track?" Then, if the patient's responses to the post-meditation survey indicate that the patient is experiencing some improvement in her anxiety, the system can select a second meditation track that targets an alternate psychological condition of the patient, such as chronic neck pain. As the patient requests additional meditation tracks over time and provides positive feedback regarding the effect of the meditation tracks on various symptoms, the system can serve to the patient additional meditation tracks that address these other symptoms in series. For example, the system can: generate a first rank of the patient's symptoms based on the results of the first psychological test, such as based on symptom or condition severity; address these symptoms in order of rank with a sequence of meditation tracks within one meditation path; and update the symptom rankings over time based on the patient's responses to post-meditation surveys. The system can therefore serve a custom sequence of meditation tracks of a variety of meditation types to the patient within one meditation path in order to guide the patient in developing a breadth of meditation-based skills and meditation-enabled emotions for managing various symptoms, improving physical and mental health, and maintaining general wellbeing based on manual feedback provided by the patient.

However, if the patient's responses to a post-meditation survey do not indicate that the patient has experienced an improvement in a symptom following a meditation track (or has not identified a tool suitable for managing a symptom following the meditation track), the system can select an alternate meditation track to address the same symptom. In the foregoing example, if the patient does not indicate that she has experienced a noticeable change in her anxiety following the first meditation track, the system can serve an additional anxiety-directed meditation track configured to address the patient's anxiety but in a different mode or pathway. For example, if the patient's responses to a post-meditation survey following the first meditation track indicate that the patient is not currently responsive to mindfulness meditation, the system can select a Pranayama meditation session in order to address the patient's anxiety with an alternate type of meditation. The system can therefore continue to address the same symptom (e.g., the patient's highest-ranking symptom) with alternate types of meditation tracks until the patient confirms some relief from this symptom based on manual feedback supplied by the patient through a post-meditation survey.

13. Second Psychological Test

Block S112 of the method recites, at a second time succeeding completion of the first meditation path by the patient, serving a second psychological test to the patient through the virtual patient portal. Generally, in Block S112, the system can implement methods and techniques similar to those of Block S110 described above to serve a second psychological test to the patient and to collect responses to this second psychological test from the patient.

In one implementation shown in FIG. 1, the system serves the same psychological test in Block S112 as served to the patient prior in Block S110 and then compares results of the second meditation path to results of the first meditation path directly to identify changes in the severity of a psychological condition affecting the patient since the first psychological test in Block S122. Alternatively, the system can serve an alternative psychological test to the patient in Block S112, such as a lower-ranked psychological test in a list of ranked psychological tests selected by a care provider.

In another implementation, the system customizes a second psychological test for the patient based on the patient's responses to the first psychological test and/or results of the first meditation path in Block S112. For example, if the patient's responses to the first psychological test indicate that the patient is experiencing high anxiety, the system can populate a second psychological test with anxiety-directed questions to further ascertain details about the patient's anxiety, such as more probing questions regarding a source of the patient's anxiety (e.g., work, school, relationship, financial stress, emotional trauma, serious medical illness, a side effect of medication, or use of an illicit drug, etc.). In a similar example, if the patient's responses to the first psychological test indicate that the patient is experiencing depression, the system can select a second psychological test containing depression-related questions to further ascertain details about the patient's depression, such as whether past abuse, adherence to a prescribed medication, external conflict, loss, genetic predisposition, illness, and/or substance abuse are contributing to the patient's depression. The system can then select a second meditation path configured to assist the patient in developing and strengthening mental tools for addressing a source of the patient's depression in Block S132.

In yet another example, if the patient's responses to the first psychological test indicate that the patient is experiencing physical pain, the system can select a second psychological test containing questions regarding the location, severity, duration, type (e.g., throbbing, dull, nauseating, shooting), causes, and/or triggers, etc. of this physical pain. In this example, the system can serve a first meditation path containing general mindfulness meditation tracks to the patient in Block S140 and then serve a second meditation path containing a body scan meditation track to the patient in Block S142 to address general areas of the patient's body where she is experiencing dull or nauseating pain, as indicated by the user in the second psychological test. Similarly, in this example, the system can serve a first meditation path containing a general mindfulness meditation track to the patient in Block S140 and then serve a second meditation path containing a Vipassana meditation track to the patient in Block S142 to address specific areas of the patient's body where she is experiencing throbbing or shooting pain, as indicated by results of the second psychological test.

However, the system can serve a second psychological test of any other type to the patient in any other way in Block S112.

14. Second Meditation Path

Block S122 of the method recites calculating new intensities of each psychological condition in the set of psychological conditions of the patient based on results of the second psychological test; and Block S132 of the method recites matching a second meditation path, from the set of predefined meditation paths, to the patient based on the new intensities of each psychological condition in the set of psychological conditions. Generally, in Blocks S122 and S132, the system can implement methods and techniques similar to those of Blocks S120 and S130 to transform responses to the second psychological test supplied by the patient into severities of psychological conditions affecting the patient and to match a meditation path to the patient based on these severities.

In one implementation, the system repeats Blocks S120 and S130 described above to transform results of the second psychological test into a ranked set of psychological conditions in Block S122 and then selects a particular meditation path—from a set of available meditation paths—configured to specifically address the highest-ranked psychological condition (or subset of psychological conditions) in the ranked set in Block S132. In this implementation, the system can match the patient to the second meditation path based on the new intensities of various psychological conditions tested in the second psychological test and regardless of results of the first psychological test or results of the first meditation path.

Alternatively, the system can match the patient to a second meditation path based on a change in severity of a psychological condition between the first psychological test and the second psychological test. For example, the system can select the first meditation path configured to address the patient's highest-priority psychological condition in Block S130 and then select a second meditation path configured to address a second psychological condition of lower rank in Block S132 if a comparison between results of the first and second psychological tests show that severity of the highest-priority psychological condition has improved over the course of the first meditation path. In particular, the system can match the patient to a second meditation path—configured to address a second psychological condition—in response to a second severity of the highest-priority psychological condition represented in results of the second psychological test falling below a first severity of the first psychological condition represented in results of the first psychological test by more than a threshold difference. The system can therefore select meditation paths configured to address the patient's lower-priority psychological conditions as psychological test results suggest improvement of higher-ranked psychological conditions.

However, if the second severity of the highest-ranked psychological condition—calculated from results of the second psychological test—is substantially similar to or greater than the first severity of the highest-ranked psychological condition—calculated from results of the first psychological test—the system can select a second meditation path containing a unique set of meditation tracks configured to again address the highest-ranked psychological condition, though differently from the first meditation path. Therefore, the system can cycle through various meditation paths configured to address the same highest-priority psychological condition of the patient in different ways as psychological test results suggest minimal improvement or worsening of the severity of this highest-ranked psychological condition over time.

14.1 Example: Anxiety+Depression

In one example, the system can: identify the patient as suffering from multiple psychological conditions including anxiety and depression based on results of the first psychological test; calculate an initial severity of depression and an initial severity of anxiety in the patient based on results of the first psychological test in Block S120; and prioritize anxiety over depression according to a psychological condition model, as described above, in Block S120. In particular, the system can prioritize the patient's anxiety over the patient's depression if the initial severity of depression is less than the initial severity of anxiety or exceeds the initial severity of anxiety by less than a threshold severity value. The system can then select a first meditation path configured to address the patient's anxiety in Block S130.

Once the patient completes the first meditation path and then completes the second psychological test, the system can: calculate a new severity of depression and a new severity of anxiety in the patient based on results of the second psychological test in Block S122; and select a second meditation path configured to address depression if the new severity of depression exceeds the new severity of anxiety by more than the threshold severity value in Block S130, such as if the patient's anxiety has lessened or if the patient's depression has increased since the first psychological test.

However, if the new severity of anxiety calculated in Block S122 approximates the initial severity of anxiety calculated in Block S120 (i.e., if the patient's anxiety has not lessened by more than a threshold value by the second psychological test), the system can select a third meditation path again configured to address the patient's anxiety and containing a unique sequence of guided meditation tracks distinct from the first meditation path. The system can thus select a second meditation path to readdress the patient's anxiety with a different set of meditation tracks if the first meditation path yields minimal improvement in the patient's anxiety.

In a similar example in which the patient is identified as suffering from both depression and anxiety, the system can populate the first meditation path with a first number of (e.g., seven) guided meditation tracks configured to predominately address anxiety and a second number of (e.g., three) guided meditation tracks—less than the first number of guided meditation tracks—configured to predominately address depression in Block S130. Following completion of the first meditation path and upon receipt of the patient's responses to the second psychological test indicating reduction in the patient's anxiety severity, the system can populate a second meditation path with a third number of (e.g., four) guided meditation tracks configured to predominately address anxiety and a fourth number of (e.g., six) guided meditation tracks configured to predominately address depression in Block S132. The system can thus match a patient to a meditation path containing sets of meditation tracks configured to address each of multiple psychological conditions affecting the patient based on the severities of these psychological conditions.

14.2 Example: PTSD+Pain

In another example, the system: identifies the patient as suffering from post-traumatic stress disorder and physical pain based on results of the first psychological test in Block S120; ranks the patient's PTSD above the patient's pain according to the psychological condition model, as described above; and then matches the patient to a first meditation path configured to address post-traumatic stress disorder in Block S130. Upon completion of the first meditation path and upon receipt of the patient's responses to the second psychological test that indicate improvement in the patient's PTSD symptoms, the system can select the second meditation path configured to address pain in Block S132. The system can also strip any guided meditation tracks relating to mindfulness—which may upset a patient with PTSD—from the second meditation path, as shown in FIG. 1. In particular, the system can remove mindfulness meditation tracks from all meditation paths assigned to the patient if the patient is identified as suffering from PTSD at any time during a treatment program or remove mindfulness meditation tracks from all meditation paths assigned to the patient while the severity of the patient's PTSD exceeds a threshold PTSD severity.

Therefore, the system can modify a meditation path configured to address one psychological condition affecting the patient based on the presence and/or severity of another psychological condition affecting the patient.

14.3 Second Meditation Path Based on Meditation Score

As shown in FIG. 1, the system can also select the second meditation path (or meditation tracks within the second meditation path) for the patient based on the patient's meditation score calculated from biometric data collected from the user during completion of one or more meditation tracks within the first meditation path. For example, if the system calculates a low composite meditation score (e.g., less than 50/100) for a meditation track previously completed by the patient and if results of the second psychological test indicate that the patient is experiencing throbbing knee pain, the system can match the patient to a second meditation path containing a three-minute beginner Vipassana meditation track with extensive audio guidance. In this example, if the system alternatively calculates an intermediate meditation score (e.g., between 50/100 and 70/100) for a meditation track previously completed by the patient and if results of the second psychological test indicate that the patient is experiencing anxiety, the system can match the patient to a second meditation path containing an eight-minute intermediate mindfulness session with limited audio guidance.

In another example, if results of the first psychological test indicate that the patient is suffering from depression due to external conflict, the system can select a first meditation path containing a sequence of inward loving kindness meditation tracks of increasing duration and difficulty for the patient in Block S110. If results of the second psychological test indicate that the patient is still suffering from depression due to external conflict but exhibited increasing meditation scores throughout the first meditation path or achieved a threshold meditation score for inward loving kindness meditation (e.g., at least a meditation score of 70/100), the system can select a second meditation path containing a sequence of outward loving kindness meditation tracks of increasing duration and difficulty for the patient in Block S132. Later, the system can select a third meditation path containing a sequence of guided mindfulness meditation tracks configured to reinforce general wellbeing in the patient once the patient has achieved a suitable mastery of loving kindness meditation, such as a meditation score of at least 80/100 for both inward and outward loving kindness meditation.

In yet another example, the system can select a first meditation path associated with a first or default difficulty level in Block S130 and then select a second meditation path associated with a greater difficulty level (e.g., contains meditation tracks of greater duration and less audio guidance) in Bock S132 if the patient's meditation score trended upwardly through the first meditation path, and vice versa.

In another example, if the severity of a psychological condition addressed in the first meditation path does not substantially change (or worsens) between the first psychological test and the second psychological test but the system calculates a relatively high meditation score for the first meditation path, the system can select a second meditation path containing a distinct combination of meditation tracks configured to address the same psychological condition in a different way than the first meditation path and of the same or greater difficulty level. The system can thus execute an alternate approach to addressing the same psychological condition in the patient if the patient's meditation score is sufficiently high—indicating the patient's ability to meditate or to enter a heightened state of mindfulness—given limited improvement in the severity of the psychological condition in the patient. However, if the severity of the psychological condition addressed in the first meditation path does not substantially change between the first psychological test and the second psychological test and the system calculates a relatively low meditation score for the first meditation path, the system can alternatively select a beginner or entry-level meditation path containing a set of meditation tracks containing more meditation guidance and/or additional instructional videos and not configured to address a specific psychological condition. The system can thus provide increased meditation guidance to the patient if the patient's meditation score is low and an estimated effect of a previous meditation path is limited. Furthermore, once the patient's meditation score increases to a threshold level, the system can reassign the first (or previous) meditation path to the patient.

The system can thus track the patient's meditation score over time and serve to the patient meditation tracks matched for the patient's current meditation skill level over time. In particular, the system can populate a meditation path with meditation tracks of a particular duration, skill level, and/or meditation type, etc. in Block S132 based on results of the second psychological test and the patient's meditation skill level, as determined from the first meditation track. The system can repeat the foregoing processes over time, such as to assign a third, fourth, fifth, and additional meditation paths to the patient based on additional psychological test results and the patient's meditation skill level in order to dynamically address varying severities of psychological conditions affecting the patient.

15. Serving the Second Meditation Path

Block S142 recites serving a second guided meditation track in the second meditation path to the patient through the virtual patient portal. Generally, in Block S142, the system can implement methods and techniques similar to those of Block S140 described above to serve meditation tracks within a meditation path to the patient, as shown in FIGS. 1, 2, and 3.

16. Interjecting Meditation Tracks

As shown in FIG. 2, one variation of the method includes: accessing a current biometric signal of the patient in Block S180; inferring a current physiological state of the patient at the third time from the current biometric signal in Block S182; selecting an alternate guided meditation track outside of the first meditation path based on an intensity of the current physiological state of the patient in Block S184; and serving the alternate guided meditation track in place of a current guided meditation track within the first meditation path through a virtual patient portal executing on the computing device in Block S186. Generally, in this variation, the system can monitor a biometric signal of the patient—such as the patient's heart rate, heart rate variability, or skin temperature—and then serve a meditation track outside of a current meditation path to address an immediate psychological state indicted by the patient's biometric signal. In particular, rather than serve a next meditation track in the current meditation path to the patient, the system can select an alternate meditation track that may be more relevant to the patient's current psychological state and serve this alternate meditation track to the patient before returning to meditation tracks within the current meditation path.

In one example, the meditation headset includes a heart rate sensor, such as in the form of a contact-based infrared pulse oximetry sensor, that monitors the patient's heart rate. (Alternatively, a mobile computing device executing the native guided meditation application can download heart rate data from a standalone wrist- or chest-borne heart rate sensor worn by the patient and wirelessly paired to the mobile computing device.) The system can then calculate the patient's current heart rate variability based on outputs of the heart rate sensor and infer the patient's current stress level as an inverse function of the patient's current heart rate variability. If the patient's current inferred stress level exceeds a threshold stress level (or if the patient's heart rate variability is less than a threshold heart rate variability), the system can select an alternate guided meditation track configured to address stress and then serve this alternate meditation track to the patient in place of a current meditation track in the patient's current meditation path (e.g., in place of a current meditation track configured to anxiety identified in a previous psychological test served to the patient). In this example, the system can continue to monitor the patient's heart rate variability during and after completion of the alternate meditation track, serve another alternate meditation track to address the patient's stress if the patient's stress remains high, and return to the current meditation track in the current meditation path if the patient's inferred stress level drops below the threshold stress level (or if the patient's heart rate variability rises above the threshold heart rate variability).

In another example, the system can also prompt the patient to enter a current mood, rank a current stress or anxiety level, enter a general wellness score, or provide any other feedback prior to serving a next meditation track to the patient, such as at the beginning of each unique meditation session. If feedback provided by the patient indicates that the patient is currently experiencing a high level of stress, anxiety, or depression etc. that may impede effectiveness of a next scheduled meditation track in the current meditation path, the system can then implement similar methods and techniques to selectively replace the next scheduled meditation track with an alternative meditation track to address this immediate condition of the patient.

The system can therefore identify and address an immediate psychological or physiological condition of the patient by injecting an alternate meditation track into the current meditation path in Blocks S180, S182, S184, and S186 in order to better prepare the patient to complete a next meditation track in the current meditation path. Once the immediate psychological or physiological condition is addressed (and reduced in intensity via an alternate meditation track), the system can return to serving meditation tracks in the current meditation path in sequential order.

17. Preoperative Meditation Path

As shown in FIG. 3, one variation of the method includes: receiving an electronic medical record of the patient indicating an upcoming scheduled surgery in Block S190; assigning a preoperative meditation path to the patient in Block S192, the preoperative meditation path comprising a set of tracks configured to address post-operative pain management; and, before the upcoming scheduled surgery, serving a guided meditation track in the preoperative meditation path to the patient through the virtual patient portal in Block S194. Generally, in Blocks S190, S192, and S194, the system can select a meditation path configured to address physical pain and then preemptively serve this meditation path to the patient in preparation for an upcoming medical surgery.

In this variation, the system can automatically retrieve an electronic medical record of the patient and scan the electronic medical record for an upcoming surgery, such as once per day, week, or month. If an upcoming surgery is identified from the electronic medical record, the system can select a preoperative meditation path to serve to the patient. For a preoperative meditation path containing a number of meditation tracks commonly completed by patients within one week, the system can serve the preoperative meditation path to the patient seven days (or eight days) prior to the scheduled surgery. Similarly, the system can estimate a duration of time for the patient to complete the preoperative meditation path based on patient meditation history (e.g., data collected during previous meditation paths served to the patient) and then serve the preoperative meditation path to the patient accordingly such that the patient may complete the preoperative meditation path just before the scheduled surgery. Alternatively, a care provider can manually enter a date and type of surgery scheduled for the patient, such as through a care provider portal, and the system can select a preoperative meditation path for the patient accordingly.

The system can also access or receive a type of the surgery scheduled for the patient and select a particular meditation path configured to address pain commonly associated with this type of surgery. For example, the system can store unique meditation paths for addressing pain common in each of back, knee, hip, gastrointestinal, heart, and brain surgeries, etc. and select a particular meditation path—from this set—corresponding to the type of surgery scheduled for the patient.

Therefore, in this variation, the system can serve a preoperative meditation path configured to aid the patient in developing tools for managing pain. Following the surgery, the patient may use meditation skills developed during the preoperative meditation path to manage her pain without or with less pain medication.

18. Additional Factors

The system can collect patient psychological condition data, patient biometric data, and other feedback over time, as described above, and store these data in a patient database. For example, the system can access diagnoses, diagnostic test results, blood test results, blood pressure, heart rate, weight change, and other patient biometric and pathological data from the patient's electronic health records or from data entered directly by doctors, therapists, and other care providers. The system can also collect patient psychological condition and biometric data through psychological tests delivered to the patient, such as patient responses to questions including: "How would you rate your anxiety today?"; "Are you avoiding painful behaviors?"; "Are you feeling good about yourself today?"; etc. delivered in a single psychological test or across multiple psychological tests over time in Blocks S110 and S112.

The system can also retrieve medication types and doses prescribed to the patient, such as from the patient's electronic health record. Alternatively, the system can prompt the patient to enter medication types and dosage data through the patient portal, such as with each psychological test. Yet alternatively, the system can interface with an electronic medication dispenser to track patient medication consumption over time.

The system can also collect patient demographic data, such as medical diagnosis history, height, race, age, gender, occupation, location, education, native language, etc. For example, the system can collect these demographic data through psychological tests issued to the patient, through patient medical record data, and through user profiles within online social networking systems.

In one variation, the system hosts an online patient forum in which patients may ask questions, answer questions, and share experiences, etc. with other patients by publishing posts in threads within the forum, such as specifically within the context of symptom management through meditation. In this variation, when a patient types a message and submits this message to the forum in the form of a post, the system can implement natural language processing to correlate words or phrases in the message with the patient's emotions, physical wellbeing, or mental wellbeing, etc. The system can therefore restructure textual data provided by the patient outside of a psychological test or clinical setting to capture more authentic and/or more nuanced post-meditation feedback for the patient; the system can store emotions, physical wellbeing, mental wellbeing, etc. extracted from these raw textual data as patient feedback. The system can implement similar methods and techniques to extract patient feedback from text communications entered into systems by the patient, such as into an online social networking system, into an email, or into a SMS text message.

The system can merge these text-based feedback data with data collected from the patient through psychological tests and from doctors, therapists, or other care providers over time to compile a breadth of feedback data from the patient before, during, and/or after a meditation path or meditation program. As described below, the system can also extract trends from these data and compare these trends to patient meditation scores and parameters of meditation tracks served to patients in order to build a meditation model linking meditation parameters, meditation tracks, meditation paths, and meditation programs to positive (and negative) patient outcomes, such as reduction in pain, other psychological symptoms, and consumption of medication.

The system can also apply patient feedback data extracted from such textual communications entered by a patient in order to define meditation parameters for a subsequent meditation path served to the patient. For example, if the patient posts a message reciting, "I thought the last few weeks of meditation were really helping my anxiety, but my son just got suspended from school, and I am really angry and stressed right now" to a meditation forum, the system can interpret this post as positive feedback for the patient's last few weeks of mindfulness meditation tracks targeting anxiety management but then interject a Pranayama meditation track into the patient's current meditation path in order to address the patient's anger in Blocks S180, S182, S184, and S186.

The system can therefore implement machine learning techniques to generate, maintain, and improve a meditation model based on patient feedback collected over time, and the system can also apply patient feedback to the meditation model in order to generate and serve customized meditation tracks that target the patient's immediate conditions and symptoms.

?. Meditation-Symptom Correlations

The system can compare patient feedback collected over time to patient meditation scores for meditation tracks served throughout a patient population over a period of time in order to correlate meditation types, meditation tracks, and/or meditation paths with particular patient outcomes, such as changes in symptom severity, pain level, degree of anxiety, etc. The system can implement these meditation type and patient outcome relationships to later define meditation parameters (e.g., type, duration, guidance level, etc.) for subsequent meditation tracks selected for patients within the patient population. In particular, the system can correlate trends in patient-entered pain level, medication consumption, anxiety, depression, attention span, blood pressure, weight, resting heart rate, and/or other psychological conditions of patients within a patient population with meditation types, meditation track durations, meditation track order within meditation programs, patient meditation scores, etc. over time to create, maintain, and update a meditation model for predicting patient outcomes based on meditation paths served to patients exhibiting a variety of psychological conditions and symptoms, and the system can pass patient-specific data into this generic meditation model to select particular meditation paths to serve to a patient. For example, the system can implement pattern recognition and/or pattern extraction, such as within a neural network, to generate new meditation paths or to modify existing meditation paths to address a particular psychological condition based on data collected from patients across the patient population.

In one implementation, the system applies masks or filters to an existing set of meditation paths to identify trends in patient meditation scores and psychological conditions of the patient. For example, the system can store a set of meditation track filters, such as including: meditation type (e.g., mindfulness, inward loving kindness, outward loving kindness, Vipassana, Zen, Mantra, Chakra, and Pranayama meditation types); meditation track duration (e.g., three to five minutes, five to ten minutes, ten to twenty minutes, twenty minutes to one hour); degree of guidance (e.g., low, moderate, high), meditation track frequency (e.g., once per week, once per day, twice per day); etc. In this example, the system can also store a set of symptom types, such as including: anxiety, depression, back pain, joint pain, substance addiction, fatigue, poor concentration, anger, etc. The system can then apply singular meditation filter values or combinations of meditation filter values to historical patient meditation scores to generate discrete meditation score trendlines, each associated with an unique meditation filter set; and the system can similarly apply a singular symptom filter or a combination of symptom filters to historical patient-entered or doctor-recorded symptom levels to generate discrete symptom level trendlines, each associated with a unique symptom filter set. The system can then calculate a confidence interval for a correlation between each meditation score trendline and each discrete symptom level trendline, record meditation-symptom trend pairs exhibiting the strongest correlations above a threshold confidence interval, and apply these correlations to future meditation path and meditation track selection in Blocks S130 and S132 described below.

In one example, the system can identify a trend in anxiety reduction within a subset of a patient population, such as based on patient responses to psychological tests, based on text entered by patients within a forum and processed with natural language processing techniques as described above, and/or based on care provider diagnoses written to patient health records. The system can then retrieve meditation scores for patients in this population subset and identify a correlation between reduction in patient anxiety and increase in patient meditation scores—for a particular meditation type for a particular set or sequence of meditation tracks—over a period of time. In this example, the system can test a correlation between trends in increasing meditation scores for patients completing an average of five mindfulness meditation tracks between seven minutes and ten minutes in length per week and reduction in reported or diagnosed anxiety levels; the system can then calculate a confidence interval for a correlation between increasing meditation scores and decreasing anxiety levels and can map daily mindfulness meditation tracks between seven minutes and ten minutes in length to reduction in anxiety if the calculated confidence interval exceeds a threshold confidence interval (e.g., above 97.5%). The system can similarly test a correlation between the same trend in increasing meditation scores for seven- to ten-minute meditation tracks and reduction in reported or diagnosed pain levels, medication dosages, anxiety, depression, and/or other symptoms by applying other symptom filters to these historical patient meditation and psychological condition data.

The system can then store and later implement these inverse correlations between meditation scores (for given types and durations of meditation tracks) and psychological condition of patients to select meditation tracks for future patients experiencing similar symptoms. For example, the system can add symptom type and symptom effect tags to nodes within a meditation decision tree and can reorder nodes within the meditation decision tree based on calculated correlations between recorded meditation score trends and recorded changes in psychological condition levels over time, as described below and shown in FIGS. 4 and 6.

The system can implement these methods and techniques across a whole patient population. Alternatively, the system can filter meditation scores and psychological condition types based on patient demographic data and then identify correlations between meditation scores and patient outcomes for subgroups of patients of similar demographic(s). For example, the system can filter meditation score and psychological condition data based on: age group (e.g., 1-5, 5-12, 12-17, 18-24, 25-34, 35-44, 45-54, 55-64, and 65+ age groups); gender; race; geographic location (e.g., rural, urban, or suburban; town, city, state, or region); occupation; marital status; genetic predisposition; medication prescriptions; medical history (e.g., surgical history, diagnosis history, genetic predisposition, etc.); height; weight; initial symptom levels; etc. The system can thus identify correlations between trends in meditation scores and symptom levels within a singular demographic subset of a population (e.g., patients between 35 and 44 years of age) or within a combination of demographic parameters within a subset of the population (e.g., male patients between 35 and 44 years of age located within the eastern United States, employed in white-collar jobs, and associated with genetic predispositions for diabetes) by applying meditation and symptom filters to historic meditation score and symptom data for patients in these demographics, as described above. The system can then apply these meditation-symptom correlations to a single meditation model (e.g., a meditation decision tree) or apply these meditation-symptom correlations to respective demographic-specific and/or symptom-specific meditation models, as described below.

The system can therefore record and analyze meditation score data, meditation parameter data, and/or psychological condition data over time—such as for a sequence of meditation tracks served to a patient within a single clinical visit or served to a patient over weeks, months, or years of clinical visits, outpatient meditation tracks, and/or home meditation tracks—to identify short- and/or long-term relationships between meditation and symptoms across a patient population.

9. Dynamic Meditation Path

Figure 6:
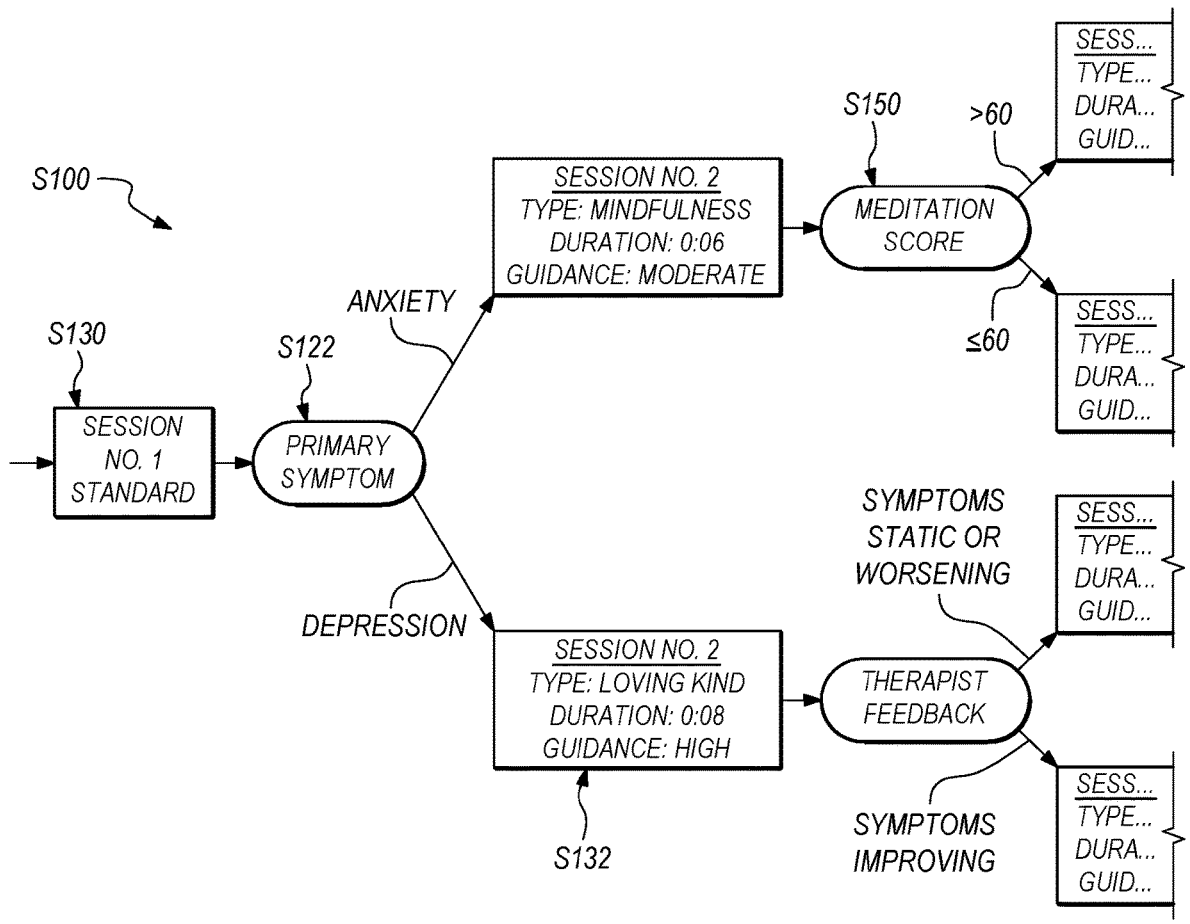
FIG. 6 is a flowchart representation of one variation of the method.

In one implementation, the system models a meditation program in the form of a decision tree including a set of nodes specifying a sequence of meditation tracks and related symptom-, meditation score-, and/or patient feedback-based triggers for navigating through these nodes, as shown in FIG. 6. For example, the system can include a single decision tree defining a start node specifying a first meditation track, and the system can serve this first meditation track to all new patients. In this example, the decision tree can also include a parallel set of secondary nodes succeeding the first node, wherein each secondary node defines a different meditation track corresponding to a particular meditation skill level (e.g., beginner, intermediate, and advanced), and the system can select one of the secondary nodes for a second meditation track for a particular patient based on the patient's meditation score from the first meditation track. In this example, the decision tree can further include a set of tertiary nodes for each secondary node, wherein each tertiary node defines a distinct meditation track selected based on: a change in the patient's meditation score between the first meditation track and a second meditation track; patient feedback regarding a change in symptom severity since the first meditation track; a patient's demographic (e.g., age, gender, weight, medical history); and/or a highest-risk symptom or combination of present symptoms; etc. The decision tree can further include quaternary nodes, quinary nodes, senary nodes, and higher-order nodes, each defining parameters of a meditation track (e.g., type, length, and degree of guidance), and the decision tree can similarly define demographic, meditation score, symptom level, and/or other triggers for moving from one node to a next node to select a subsequent meditation track for a patient.

The system can thus implement a single unilateral (e.g., one-direction), multilateral, or multi-dimensional decision tree, such as defining tens, hundreds, or thousands of nodes, each associated with a set of meditation track parameters and linked vertically or horizontally with one or more adjacent or distant other nodes via demographic, meditation score, symptom level, and/or other triggers, and the system can pass current and/or historical patient meditation, symptom, and/or demographic data into the singular decision tree to select each subsequent meditation track for a patient. The system can also maintain multiple discrete decision trees, such as: one for each age bracket; one for each disease or symptom type; one for men and one for women; etc., and the system can select an appropriate decision tree for a patient when selecting and serving a new meditation track to the patient.

In this implementation, the system can also update or modify the decision tree(s) over time based on determined correlations between patient meditation scores, parameters of meditation tracks served to patients, and patient outcomes (e.g., changes in symptom severities) across a patient population, as described above. For example, based on meditation/symptom correlations extrapolated from short-term and/or long-term patient data, the system can: reroute links between nodes to rearrange an order of meditation tracks within a meditation path (as shown in FIG. 4); add or remove nodes within the decision tree; assign alternate triggers to links between nodes (e.g., meditation score, absolute or relative symptom progression, patient demographic data, etc.); modify trigger magnitudes of links between nodes; etc. in order to improve the decision tree over time or to customize the decision tree for a patient population or for a particular patient. In particular, the system can implement supervised machine learning techniques to transform patient feedback—gathered through psychological tests, analysis of social media or forum content entered by patients, doctor- or therapist-entered reports, etc.—and meditation scores for patient-performed meditation tracks into a meditation model and to improve the meditation model over time. The system can therefore implement past patient data within a dynamic meditation model to improve customization of meditation tracks (e.g., tailored meditation types, durations, guidance, etc.) served to patients given each patient's past, current, and/or predicted future symptom severity, physical health, mental health, and overall wellbeing in Block S170.

However, the system can implement any other suitable type of meditation model, such as Markov chains, Morphological analysis, an influence diagram, etc., to define meditation track parameters and patient triggers within a meditation program. The system can then apply data collected from a patient—such as directly from the patient via psychological tests, meditation forum posts, etc. or from the patient's care provider—to serve meditation tracks customized for the patient over time based on the patent's current immediate condition, needs, symptoms, etc.

The system can implement similar methods and techniques to generate and apply a decision tree to select complete, static meditation paths—within a greater meditation program—for a patient.

10. Biofeedback Therapy

The system can implement similar methods and techniques to select and serve biofeedback therapy sessions, hypnosis sessions, or other wellness programs to a patient over time, such as in addition to or instead of meditation tracks. In one implementation, the system selects and serves biofeedback therapy sessions to a patient over time (a "custom biofeedback program") to train the patient to control physiological processes, such as muscle tension, blood pressure, heart rate, heart rate variability, or other generally involuntarily physiological processes. In this variation, the system can interface with various sensors, such as a skin temperature sensor, a blood pressure sensor, a pulse oximetry sensor, a heart rate sensor, a heart rate variability sensor, a vibratory sensor, a muscle tension sensor, an electromyography (EMG) sensor, and/or an EEG sensor, etc. (instead of or in addition to a meditation headset) integrated into one or more wearable devices to track the patient's vital signs, physiological state, and/or physiological functions before, during, and/or after a biofeedback therapy session. The system can then merge these data with a biofeedback therapy model (e.g., a meditation-based biofeedback therapy model or a heart rate variability-based biofeedback model) to track the patient's development of biofeedback therapy skills and to serve new biofeedback therapy sessions to the patient, such as biofeedback therapy sessions selected from a set of deep breathing sessions, progressive muscle relaxation sessions, guided imagery-type meditation tracks, and mindfulness-type meditation tracks.

The system and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for automatically prescribing guided meditation based on biometric signals of a patient, the method comprising:

serving a first psychological test to the patient through a virtual patient portal executing on a computing device;

transforming results of the first psychological test into a set of psychological conditions of the patient;
matching intensities of psychological conditions in the set of psychological conditions to a particular template psychological test result in a set of template psychological test results;
assigning a first meditation path, from a set of predefined meditation paths, to the patient based on a severity of each psychological condition in the set of psychological conditions, the first mediation path associated with the particular template psychological test result;
at a first time, serving a first guided meditation track in the first meditation path to the patient through the virtual patient portal;
calculating a meditation score comprising a quantitative value inversely proportional to a magnitude of alpha waves read from an electroencephalography headset worn by the patient during completion of the first meditation path by the patient;
at a second time succeeding completion of the first meditation path by the patient, serving a second psychological test to the patient through the virtual patient portal;
calculating new intensities of each psychological condition in the set of psychological conditions of the patient based on results of the second psychological test;
matching a second meditation path, from the set of predefined meditation paths, to the patient based on the new intensities of each psychological condition in the set of psychological conditions and the meditation score; and
at a third time succeeding the second time, serving a second guided meditation track in the second meditation path to the patient through the virtual patient portal.

2. The method of claim 1:
wherein assigning the first meditation path to the patient comprises selecting the first meditation path associated with a first difficulty level;
wherein matching the second meditation path to the patient comprises selecting the second meditation path associated with a second difficulty level greater than the first difficulty level in response to the meditation score of the patient trending upwardly through the first meditation path.

3. The method of claim 1:
wherein calculating the meditation score comprises, at the computing device, downloading electroencephalography data from the electroencephalography headset during completion of the first guided meditation track in the first meditation path by the patient at a medical facility; and
further comprising, at a personal mobile computing device carried by the patient, serving a survey prompting the patient to indicate severity of a psychological condition in the set of psychological conditions following completion of a second guided meditation track in the first meditation path by the user outside of the medical facility.

4. The method of claim 1:
wherein transforming results of the first psychological test into the set of psychological conditions of the patient comprises identifying the patient as affected by psychological conditions comprising post-traumatic stress disorder and physical pain based on results of the first psychological test;
wherein matching the first meditation path to the patient comprises selecting the first meditation path configured to address post-traumatic stress disorder;
wherein matching the second meditation path to the patient comprises:
selecting the second meditation path configured to address pain; and
stripping guided meditation tracks relating to mindfulness from the second meditation path in response to a new severity of post-traumatic stress disorder in the patient, calculated from the second psychological test, exceeding a threshold post-traumatic stress disorder severity.

5. The method of claim 1:
further comprising: receiving an electronic medical record of the patient indicating an upcoming scheduled surgery;
assigning a preoperative meditation path to the patient, the preoperative meditation path comprising a set of tracks configured to address post-operative physical pain; and
at a fourth time preceding the upcoming scheduled surgery, serving a guided meditation track in the preoperative meditation path to the patient through the virtual patient portal.

6. The method of claim 1:
wherein matching the patient to the first meditation path comprises matching the patient to the first meditation path comprising a first set of meditation teaching modules and guided meditation tracks configured to predominately address a primary condition represented in the first psychological test; and
wherein serving the first guided meditation track in the first meditation path to the patient comprises sequentially serving each guided meditation track in the first meditation path through the virtual patient portal as the patient completes each successive guided meditation track in the first meditation path prior to the second time.

7. The method of claim 6, further comprising:
at a third time succeeding the second time, accessing a current biometric signal of the patient;
inferring a current physiological state of the patient at the third time from the current biometric signal;
selecting an alternate guided meditation track outside of the second meditation path based on an intensity of the current physiological state of the patient; and
at approximately the third time, serving the alternate guided meditation track in place of a second guided meditation track within the second meditation path to the patient through the virtual patient portal.

8. The method of claim 7:
wherein accessing the current biometric signal of the patient comprises calculating a current heart rate variability of the patient based on outputs of a contact sensor worn by the patient;
wherein inferring the current physiological state of the patient comprises inferring a current stress level in the patient as an inverse function of the current heart rate variability of the patient; and
wherein selecting the alternate guided meditation track outside of the second meditation path comprises selecting the alternate guided meditation track in response to the current stress level in the patient exceeding a threshold stress level.

9. The method of claim 1, wherein serving the first psychological test to the patient comprises serving a validated psychological test selected from the group consisting of: a post-traumatic stress disorder test; an alcohol-abuse screening test; a substance-abuse screening test; a pain self efficacy test; an insomnia test; an opioid risk screening test; an anxiety test; a depression test; and a perceived stress test to the patient through the virtual patient portal.

10. A method for automatically prescribing guided meditation based on biometric signals of a patient, the method comprising:
serving a first psychological test to the patient through a virtual patient portal executing on a computing device;
identifying the patient as affected by psychological conditions comprising anxiety and depression based on results of the first psychological test;
calculating a first severity of depression in the patient based on results of the first psychological test;
calculating a first severity of anxiety in the patient based on results of the first psychological test;
selecting the first meditation path configured to address anxiety in response to the first severity of depression exceeding the first severity of anxiety by less than a threshold severity value;
at a first time, serving a first guided meditation track in the first meditation path to the patient through the virtual patient portal;
calculating a meditation score comprising a quantitative value inversely proportional to a magnitude of alpha waves read from an electroencephalography headset worn by the patient during completion of the first meditation path by the patient;
at a second time succeeding completion of the first meditation path by the patient, serving a second psychological test to the patient through the virtual patient portal;
calculating new intensities of the psychological conditions based on results of the second psychological test;
calculating a second severity of depression in the patient based on results of the second psychological test;
calculating a second severity of anxiety in the patient based on results of the second psychological test;
selecting a second meditation path configured to address depression in response to the second severity of depression exceeding the second severity of anxiety by more than the threshold severity value and based on the meditation score; and
at a third time succeeding the second time, serving a second guided meditation track in the second meditation path to the patient through the virtual patient portal.

11. The method of claim 10:
wherein calculating the meditation score comprises, at the computing device, downloading electroencephalography data from the electroencephalography headset during completion of the first guided meditation track in the first meditation path by the patient at a medical facility; and
further comprising, at a personal mobile computing device carried by the patient, serving a survey prompting the patient to indicate severity of a psychological condition in the set of psychological conditions following completion of a second guided meditation track in the first meditation path by the user outside of the medical facility.

12. The method of claim 10, further comprising selecting a third meditation path configured to address anxiety in response to the second severity of anxiety approximating the first severity of anxiety, the third meditation path comprising a third set of guided meditation tracks comprising more meditation guidance than guided meditation tracks contained in the first meditation path.

13. The method of claim 10:
further comprising: receiving an electronic medical record of the patient indicating an upcoming scheduled surgery;
assigning a preoperative meditation path to the patient, the preoperative meditation path comprising a set of tracks configured to address post-operative physical pain; and
at a fourth time preceding the upcoming scheduled surgery, serving a guided meditation track in the preoperative meditation path to the patient through the virtual patient portal.

14. The method of claim 10, further comprising:
at a third time succeeding the second time, accessing a current biometric signal of the patient;
inferring a current physiological state of the patient at the third time from the current biometric signal;
selecting an alternate guided meditation track outside of the second meditation path based on an intensity of the current physiological state of the patient; and
at approximately the third time, serving the alternate guided meditation track in place of a second guided meditation track within the second meditation path to the patient through the virtual patient portal.

15. The method of claim 14, further comprising:
wherein accessing the current biometric signal of the patient comprises calculating a current heart rate variability of the patient based on outputs of a contact sensor worn by the patient;
wherein inferring the current physiological state of the patient comprises inferring a current stress level in the patient as an inverse function of the current heart rate variability of the patient; and
wherein selecting the alternate guided meditation track outside of the second meditation path comprises selecting the alternate guided meditation track in response to the current stress level in the patient exceeding a threshold stress level.

16. A method for automatically prescribing guided meditation based on biometric signals of a patient, the method comprising:
serving a first psychological test to the patient through a virtual patient portal executing on a computing device;
identifying the patient as affected by psychological conditions comprising anxiety and depression based on results of the first psychological test;
populating a first meditation path with a first number of guided meditation tracks configured to predominately address anxiety and a second number of guided meditation tracks, less than the first number of guided meditation tracks, configured to predominately address depression;
at a first time, serving a first guided meditation track in the first meditation path to the patient through the virtual patient portal;
calculating a meditation score comprising a quantitative value inversely proportional to a magnitude of alpha waves read from an electroencephalography headset worn by the patient during completion of the first meditation path by the patient;
at a second time succeeding completion of the first meditation path by the patient, serving a second psychological test to the patient through the virtual patient portal;

calculating new intensities of each psychological condition in the set of psychological conditions of the patient based on results of the second psychological test;

populating a second meditation path with a third number of guided meditation tracks configured to predominately address depression and a fourth number of guided meditation tracks, less than the third number of guided meditation tracks, configured to predominately address anxiety in response to the second psychological test indicating reduction in anxiety severity and based on the meditation score; and at a third time succeeding the second time, serving a second guided meditation track in the second meditation path to the patient through the virtual patient portal.

17. The method of claim 16:

wherein calculating the meditation score comprises, at the computing device, downloading electroencephalography data from the electroencephalography headset during completion of the first guided meditation track in the first meditation path by the patient at a medical facility; and further comprising, at a personal mobile computing device carried by the patient, serving a survey prompting the patient to indicate severity of a psychological condition in the set of psychological conditions following completion of a second guided meditation track in the first meditation path by the user outside of the medical facility.

18. The method of claim 16 further comprising:

receiving an electronic medical record of the patient indicating an upcoming scheduled surgery;

assigning a preoperative meditation path to the patient, the preoperative meditation path comprising a set of tracks configured to address post-operative physical pain; and at a fourth time preceding the upcoming scheduled surgery, serving a guided meditation track in the preoperative meditation path to the patient through the virtual patient portal.

19. The method of claim 16, further comprising:

at a third time succeeding the second time, accessing a current biometric signal of the patient;

inferring a current physiological state of the patient at the third time from the current biometric signal;

selecting an alternate guided meditation track outside of the second meditation path based on an intensity of the current physiological state of the patient; and at approximately the third time, serving the alternate guided meditation track in place of a second guided meditation track within the second meditation path to the patient through the virtual patient portal.

20. The method of claim 19:

wherein accessing the current biometric signal of the patient comprises calculating a current heart rate variability of the patient based on outputs of a contact sensor worn by the patient;

wherein inferring the current physiological state of the patient comprises inferring a current stress level in the patient as an inverse function of the current heart rate variability of the patient; and wherein selecting the alternate guided meditation track outside of the second meditation path comprises selecting the alternate guided meditation track in response to the current stress level in the patient exceeding a threshold stress level.

* * * * *